(12) United States Patent
Takai et al.

(10) Patent No.: US 9,075,032 B2
(45) Date of Patent: Jul. 7, 2015

(54) TRANSPORT APPARATUS, TRANSPORT METHOD, TRANSPORT PROGRAM, AND TRANSPORT SYSTEM

(75) Inventors: Eiji Takai, Kyoto (JP); Noriaki Furusato, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 458 days.

(21) Appl. No.: 13/638,483

(22) PCT Filed: Mar. 28, 2011

(86) PCT No.: PCT/JP2011/057632
§ 371 (c)(1),
(2), (4) Date: Oct. 17, 2012

(87) PCT Pub. No.: WO2011/122557
PCT Pub. Date: Oct. 6, 2011

(65) Prior Publication Data
US 2013/0131859 A1 May 23, 2013

(30) Foreign Application Priority Data
Mar. 30, 2010 (JP) ................................. 2010-079156

(51) Int. Cl.
*G06F 7/00* (2006.01)
*G01N 35/02* (2006.01)
(Continued)

(52) U.S. Cl.
CPC ............ *G01N 35/02* (2013.01); *G01N 35/0092* (2013.01); *G01N 35/026* (2013.01); *G01N 2035/00752* (2013.01); *G01N 2035/0415* (2013.01); *B65G 43/00* (2013.01)

(58) Field of Classification Search
CPC . G11B 17/225; G11B 15/689; G11B 15/6835
USPC ........................................................ 700/214
See application file for complete search history.

(56) References Cited

U.S. PATENT DOCUMENTS

| 5,876,670 A | 3/1999 | Mitsumaki et al. |
| 2003/0092186 A1* | 5/2003 | Pressman et al. ............... 436/46 |

(Continued)

FOREIGN PATENT DOCUMENTS

| CN | 101520463 A | 9/2009 |
| JP | 01-311278 A | 12/1989 |

(Continued)

OTHER PUBLICATIONS

International Search Report; PCT/JP2011/057632; Jun. 14, 2011.
(Continued)

*Primary Examiner* — Gene Crawford
*Assistant Examiner* — Kyle Logan
(74) *Attorney, Agent, or Firm* — Studebaker & Brackett PC

(57) ABSTRACT

A transport apparatus for transporting a sample as an analysis objective in a state of being accommodated in a sample container comprises a judging unit which judges whether or not the sample container is positioned at each of first and second collection positions for collecting the sample from the sample container in order to perform each of first and second analysis processes and which outputs each of judgment results thereof as first and second collection position data; and a sample container identification unit which performs individual identification of the sample container in a transport route for the sample container and which outputs an identification result thereof as individual identification data. Further, it is confirmed whether or not the transport of the sample container to the second collection position is adequate on the basis of the first collection position data, the second collection position data, the individual identification data, and data to indicate a predetermined transport amount calculated in accordance with the first and second collection positions.

22 Claims, 6 Drawing Sheets

(51) Int. Cl.
  *G01N 35/00* (2006.01)
  *B65G 43/00* (2006.01)
  *G01N 35/04* (2006.01)

(56) References Cited

U.S. PATENT DOCUMENTS

| 2005/0070019 A1* | 3/2005 | Yamamoto | 436/43 |
| 2009/0220379 A1 | 9/2009 | Wakamiya et al. | |
| 2010/0112703 A1* | 5/2010 | Tanaka | 436/47 |
| 2010/0152890 A1* | 6/2010 | Hamada et al. | 700/230 |
| 2011/0112683 A1* | 5/2011 | Pedrazzini | 700/218 |

FOREIGN PATENT DOCUMENTS

| JP | 07-092171 A | 4/1995 |
| JP | 09-054096 A | 2/1997 |
| JP | 09-304396 A | 11/1997 |
| JP | 10-019899 A | 1/1998 |
| JP | 11-023581 A | 1/1999 |
| JP | 11-316237 A | 11/1999 |
| JP | 11-316238 A | 11/1999 |
| JP | 2003-083995 A | 3/2003 |
| JP | 2007-322289 A | 12/2007 |

OTHER PUBLICATIONS

Notification of Transmittal of copies of translation of the International Preliminary Report on Patentability and the translation of the Written Opinion of the International Searching Authority mailed on Nov. 22, 2012, which corresponds to PCT/JP2011/057632 and is related to U.S. Appl. No. 13/638,483.
The first Office Action issued by the State Intellectual Property Office of People's Republic of China on Nov. 19, 2013, which corresponds to Chinese Patent Application No. 201180016749.X and is related to U.S. Appl. No. 13/638,483.

* cited by examiner

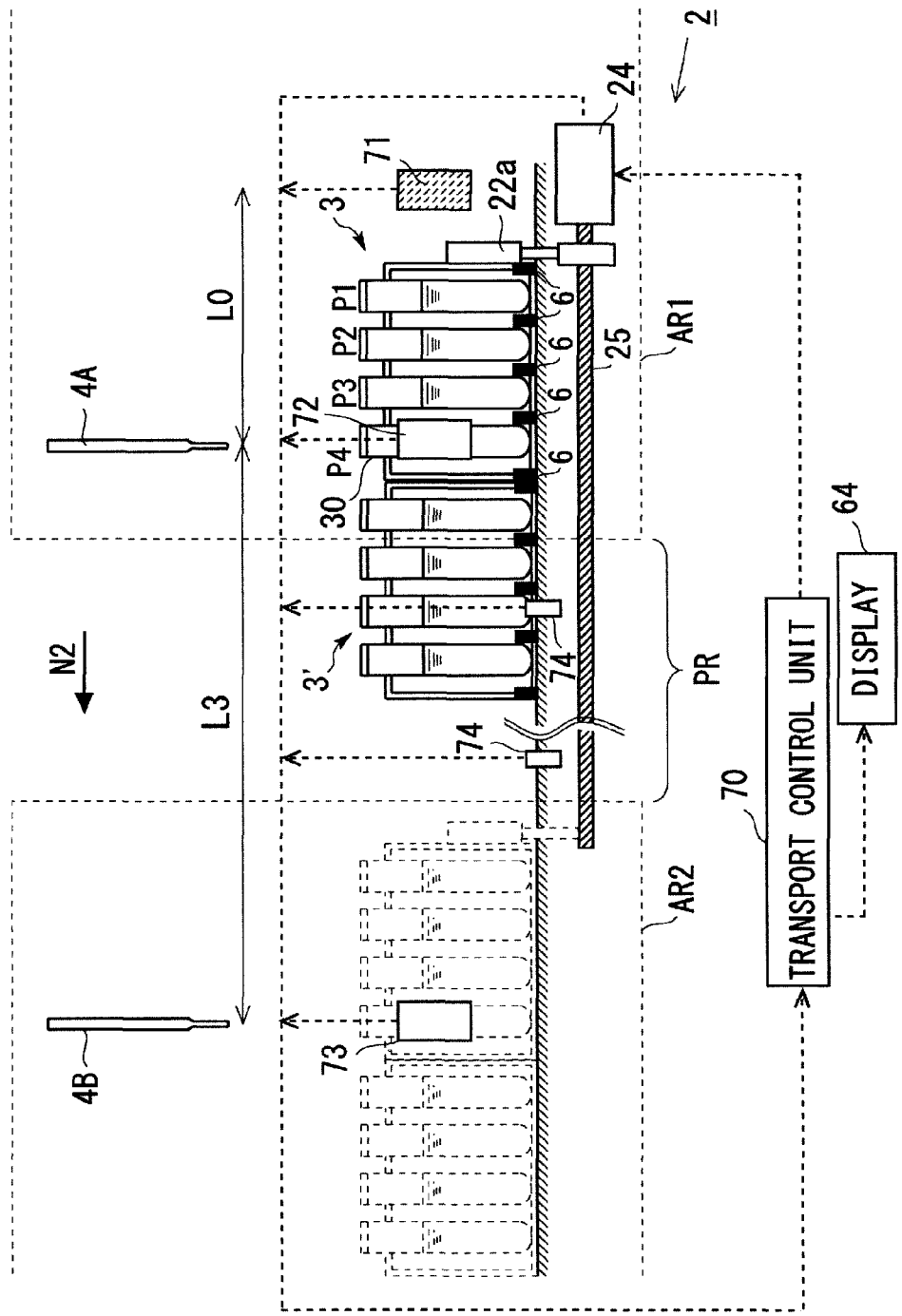

TRANSPORT APPARATUS, TRANSPORT METHOD, TRANSPORT PROGRAM, AND TRANSPORT SYSTEM

CROSS-REFERENCE TO RELATED APPLICATION

This application is the U.S. National Phase under 35 U.S.C. §371 of International Application PCT/JP2011/057632, filed on Mar. 28, 2011, which claims priority to JP Application No. 2010-079156, filed on Mar. 30, 2010, the contents of which are herein wholly incorporated by reference.

TECHNICAL FIELD

The present invention relates to a transport apparatus, a transport method, a transport program, and a transport system wherein a sample as an analysis objective is transported in a state of being accommodated in a sample container.

BACKGROUND ART

When a sample such as blood, urine or the like is analyzed, a plurality of analysis apparatuses are used in some cases depending on an object of analysis of a user. In such a situation, when the analysis is performed with respect to all of analysis items for which the respective analysis apparatuses are responsible, it is necessary that the sample should be successively transported to all of the analysis apparatuses. On the other hand, another procedure is sometimes adopted such that predetermined analysis is performed by means of a certain analysis apparatus, and it is determined whether or not analysis is carried out by means of another analysis apparatus, depending on an obtained result. When it is intended to analyze a sample while moving among a plurality of analysis apparatuses as described above, a variety of sample transport techniques have been disclosed (see, for example, Patent Documents 1 to 3), for example, in order to reduce the time required for the analysis.

In the case of the technique described in Patent Document 1, for example, the order of sample transport is adjusted taking the processing ability of each of analysis apparatuses into consideration, i.e., taking the time required for the analysis into consideration, in a system in which the plurality of analysis apparatuses are arranged. On the other hand, in the case of the techniques described in Patent Documents 2 and 3, such an arrangement or system is disclosed that samples are allowed to successively move or travel (flow) on an analysis apparatus having a plurality of analysis modules, wherein a sample, which is not to be analyzed by a certain measurement module, progresses beyond the order of analysis during a period in which another sample is analyzed by the certain measurement module in some cases, and a sample, which is to be subjected to specified analysis, is dealt with such that the concerning sample is taken into a take-in area provided on the apparatus from a main flow of the sample transport to perform the analysis in other cases.

PRECEDING TECHNICAL DOCUMENTS

Patent Documents

Patent Document 1: JP07-92171A;
Patent Document 2: JP3031242B2;
Patent Document 3: JP3031374B2.

SUMMARY OF THE INVENTION

Task to be Solved by the Invention

In order to apply various types of analysis to a sample in response to the need of a user, such an arrangement or system is adopted that a plurality of analysis apparatuses, especially a plurality of analysis apparatuses having different functions are provided in a series of flow of analysis procedures, and the analysis, which responds to the necessity, is executed. In such a situation, the information management, which includes, for example, the management of the analysis result and the individual identification of the sample, has been hitherto performed for each of the analysis apparatuses. Therefore, when a plurality of analysis apparatuses are collected or aggregated into one unit, the labor, which is required for the information management, is increased depending on the collection scale (aggregation scale).

In another viewpoint, the sample misidentification is an error which should be never caused in the analysis of the sample such as blood, urine or the like, for which the perfect countermeasure should be adopted. However, when it is intended to perform a series of analysis procedures in the flow in which a plurality of analysis apparatuses are arranged, the risk of sample misidentification cannot be eliminated during the sample transport performed between the analysis apparatus and the analysis apparatus, especially when it is intended to exchange the sample transport order among the analysis apparatuses as described in the conventional technique. On the other hand, an identifying device or apparatus, which identifies the individual of the sample, can be installed to each of the analysis apparatuses as well in order to avoid the sample misidentification. However, in this case, the number of the identifying devices is increased depending on the number of the analysis apparatuses. Therefore, the installation space for installing the system and the apparatuses for performing a series of analysis procedures is increased in some cases, and the production cost becomes expensive in other cases. As a result, the merit, which is to be obtained by collecting or aggregating the analysis apparatuses for performing a series of analysis procedures into one unit, is decreased.

The present invention has been made taking the foregoing problem into consideration, an object of which is to provide a sample transport apparatus, a transport method, a transport program, and a transport system which make it possible to realize a compact size of an entire apparatus for performing a series of analysis procedures and reliably avoid the sample misidentification when the series of analysis procedures including a plurality of analysis procedures are performed.

Solution for the Task

In order to solve the problem as described above, the present invention is constructed as follows. That is, a judging unit, which judges whether or not a sample is positioned, is provided at each of a first collection position at which the sample is collected in order to perform a first analysis process and a second collection position at which the sample is collected in order to perform a second analysis process, wherein it is reliably detected that the sample is transported from the first collection position to the second collection position by taking respective judgment results obtained thereby, a result of individual identification of the sample, and a predetermined transport amount provided when the transport is performed from the first collection position to the second collection position into consideration. Accordingly, when a series of analysis procedures including a plurality of analysis procedures are performed, then it is possible to reliably avoid the misidentification of the sample, and it is possible to realize a compact size or dimension of an entire apparatus for performing the analysis.

In view of the above, the present invention is firstly grasped from an aspect of a transport apparatus. In particular, the present invention resides in a transport apparatus for transporting a sample as an analysis objective in a state of being accommodated in a sample container; the transport apparatus comprising a first judging unit which judges whether or not the sample container is positioned at a first collection position for collecting the sample from the sample container in order to perform a first analysis process and which outputs a judgment result thereof as first collection position data; a second judging unit which judges whether or not the sample container is positioned at a second collection position for collecting the sample from the sample container in order to perform a second analysis process and which outputs a judgment result thereof as second collection position data; a container transport unit which successively transports the sample container to the first collection position and the second collection position; a sample container identification unit which performs individual identification of the sample container in a transport route for the sample container and which outputs an identification result thereof as individual identification data; and a transport confirming unit which confirms whether or not the transport of the sample container to the second collection position is adequate on the basis of the first collection position data, the second collection position data, the individual identification data, and data to indicate a predetermined transport amount calculated in accordance with the first collection position and the second collection position.

In the transport apparatus according to the present invention, the first collection position data outputted from the first judging unit and the second collection position data outputted from the second judging unit are used to judge whether or not the transport of the sample from the first collection position to the second collection position is adequate. Each of the first collection position and the second collection position is such a place that the sample is collected from the sample container in which the sample is accommodated, in order to perform each of the specified analysis processes. The collection positions are different positions. However, the analysis processes, which are applied to the sample collected at the respective positions, may be either identical with each other or different from each other. Respective pieces of the collection position data, which are outputted from the respective judging units corresponding to the respective collection positions, are the data having the contents in relation to the judgment result about whether or not the sample container, which accommodates the sample as the objective, is positioned at the position at which the sample is to be collected. In other words, each of the collection position data is the data which makes it possible to confirm the presence of the sample.

Further, in the transport apparatus according to the present invention, the individual identification data and the data to indicate the predetermined transport amount are used to judge whether or not the transport is adequate, in addition to the respective pieces of the collection position data described above. The individual identification data is the data which makes it possible to identify the individual of the sample container for accommodating the sample. As for the specified mode or embodiment thereof, it is possible to adopt various forms concerning the conventional technique. For example, it is also allowable to use the bar code technique. The data to indicate the predetermined transport amount is the data which relates to the transport amount provided to transport the sample container from the first collection position to the second collection position, as determined from the relationship between the first collection position and the second collection position. In other words, the data relates to the actual distance for transporting the sample container between the different analysis apparatuses for which the collection or sampling of the sample is actually performed in an actual analysis form for analyzing the sample.

In the transport apparatus described above, the transport confirming unit confirms whether or not the sample container, which is specified in accordance with the individual identification data of the sample container for accommodating the sample and which is subjected to the first analysis process and the second analysis process, is adequately transported to the second collection position, on the basis of the first collection position data, the second collection position data, and the data to indicate the predetermined transport amount. That is, if any correlation, in which the consistency is not maintained, is found between the presence or absence of the existence of the sample as obtained from the first collection position data and the second collection position data and the predetermined transport amount as the transport amount by which the sample container is actually transported, it is judged that the sample container, which accommodates the sample, is not normally transported from the first collection position to the second collection position. In this way, it is possible to confirm the normal transport of the sample container subjected to the individual identification in the transport apparatus as described above, by taking the correlation between the first collection position data and the second collection position data and the data to indicate the predetermined transport amount into consideration. Further, the first collection position data, the second collection position data, and the individual identification data are processed in the form of the electrical data by the transport confirming unit. Therefore, it is possible to quickly judge whether or not the transport is adequate. Further, the individual identification data is outputted by the sample container identification unit in this arrangement. The concerning identification unit is not provided for each of the collection positions for performing the analysis processes in this arrangement. Therefore, the arrangement or structure of the transport apparatus can be made relatively compact, and the cost required for the arrangement or structure can be suppressed.

The transport apparatus as described above may be constructed or arranged such that the sample container identification unit is provided on an upstream side from the first collection position in the transport route for the sample container. When the transport apparatus is constructed as described above, then the sample is collected at the first collection position and the second collection position with respect to the sample container for which the individual identification has been performed at first, and it is judged whether or not the transport from the first collection position to the second collection position is adequate as described above. As a result, it is possible to avoid the sample misidentification more reliably in the series of analysis procedures.

The transport apparatus as described above may be constructed or arranged such that the container transport unit transmits a force to successively transport the sample container to the first collection position and the second collection position via a contact portion formed between the container transport unit and the sample container. When the arrangement, in which the sample container is transported via the contact portion, is adopted, then the arrangement itself concerning the transport can be simplified, and the size of the transport apparatus itself can be made more compact. On the other hand, the transport form, in which the transport is performed by the aid of the contact portion, involves such a possibility that the sample container may be transported inadequately, if the contact state at the contact portion is not retained for any reason (for example, any unexpected contact caused by a person in charge of analysis). However, in the case of the transport apparatus according to the present invention, it is confirmed by the transport confirming unit whether or not the transport is adequate as described above. Accordingly, if the sample container is not transported adequately, the presence of inadequate transport can be reliably detected. Therefore, it is possible to avoid the possibility of the sample misidentification beforehand.

The transport apparatus as described above may be constructed or arranged such that the transport confirming unit judges that the sample container is normally transported to the second collection position if the second collection position data is data which indicates that the sample container is positioned at the second collection position, and the transport confirming unit judges that the sample container is not normally transported to the second collection position if the second collection position data is data which indicates that the sample container is not positioned at the second collection position. This construction or arrangement is a specified example of the mode or form of confirmation in relation to the confirmation performed by the transport confirming unit to confirm whether or not the transport is adequate.

The transport apparatus, in which the sample container is transported by the aid of the contact portion as described above, may be constructed or arranged such that the transport apparatus further comprises a contact portion confirming unit which confirms whether or not such a state is given that the contact portion is formed between the container transport unit and the sample container. In this case, the transport confirming unit judges that the sample container is not normally transported to the second collection position irrelevant to contents of the second collection position data, if it is judged by the contact portion confirming unit that the contact portion is not formed. If it is judged by the contact portion confirming unit that the contact portion is not formed, there is such a possibility that the adequate transport is not performed for any reason. Therefore, in order to avoid the sample misidentification more reliably as well, it is judged half-forcibly that the normal transport is not performed in the situation as described above, irrelevant to the contents of the second collection position data, for example, even if the second collection position data has the contents to indicate the presence of the sample container at the second collection position.

The transport apparatus as described above may be constructed or arranged such that the contact portion confirming unit makes the judgment in relation to the formation of the contact portion on the basis of an amount of movement of the container transport unit itself during a period in which the transport is performed by the container transport unit. When the container transport unit transports the sample container by the aid of the contact portion, the sample container and the container transport unit are moved practically in an integrated manner by the aid of the contact portion. Therefore, the state of formation of the contact portion, which greatly affects the normal transport, can be judged on the basis of the amount of movement of the container transport unit itself. For example, it is also appropriate to adopt the following arrangement. That is, when the transport apparatus further comprises a movement amount detecting unit which is provided at a passage portion for allowing the sample container transported by the container transport unit to pass therethrough between the first collection position and the second collection position and which detects the amount of movement of the sample container in the passage portion; the contact portion confirming unit further makes the judgment in relation to the formation of the contact portion on the basis of the amount of movement detected by the movement amount detecting unit, in addition to the amount of movement of the container transport unit itself.

In the transport apparatus as described above, it is also preferable that at least any one collection position of the first collection position and the second collection position is changeable in a transport direction in which the transport is performed by the container transport unit. Owing to the fact that the collection position is changeable, the collection of the sample from the sample container can be carried out in a flexible manner, which is considered to contribute to the improvement in efficiency of the sample analysis. When the collection position can be changed as described above, the data, which indicates the predetermined transport amount to be used for allowing the transport confirming unit to confirm whether or not the transport is adequate, should be the data which relates to the predetermined transport amount that reflects the changed collection position.

The transport apparatus, in which the sample container is transported by the aid of the contact portion, may be constructed or arranged such that the container transport unit simultaneously transports the sample container and another sample container by allowing a pressing force to act by making contact with the sample container from a backward position in the transport direction while bringing the sample container and the another sample container different from the sample container in contact with each other at a frontward position in the transport direction of the sample container. When the transport apparatus is constructed such that the plurality of sample containers are simultaneously transported, it is possible to allow a larger number of sample containers to undergo the flow of the series of analysis procedures. Thus, it is considered to contribute to the improvement in efficiency of the sample analysis.

When the transport apparatus further comprises a contact state detecting unit which detects a contact state between the sample container and the another sample container; the transport confirming unit may judge that the sample container is not normally transported to the second collection position irrelevant to contents of the second collection position data if an amount of movement of the sample container is different from an amount of movement of the another sample container when the transport is performed by the container transport unit after it is detected by the contact state detecting unit that the sample container and the another sample container are brought in contact with each other. If the contact state between the sample containers is not formed properly or appropriately, it is difficult to affirm that the transport of the sample container is carried out properly or appropriately. In such a situation, it is feared that the sample misidentification may occur. In view of the above, in order to avoid the sample misidentification more reliably, if it is judged that the amounts of movement of the sample containers are different from each other after the contact between the sample containers has been once confirmed, it is considered that the contact state between the both is not maintained properly or appropriately. It is judged half-forcibly that the transport is not performed normally irrelevant to the contents of the second collection position data.

The present invention can be also grasped from an aspect of a transport method as follows. That is, the present invention resides in a transport method for transporting a sample as an analysis objective in a state of being accommodated in a sample container; the transport method comprising a sample container identifying step of performing individual identification of the sample container to output an identification result thereof as individual identification data; a first judging step of judging whether or not the sample container is positioned at a first collection position for collecting the sample from the sample container in order to perform a first analysis process to output a judgment result thereof as first collection position data; a transport step of transporting, from the first collection position to a second collection position, the sample container judged to be positioned at the first collection position in the first judging step by a predetermined transport amount calculated in accordance with the first collection position and the second collection position for collecting the sample from the sample container in order to perform a second analysis process; a second judging step of judging whether or not the sample container is positioned at the second collection position in relation to the sample container transported in the transport step to output a judgment result thereof as second collection position data; and a transport confirming step of confirming whether or not the transport of the sample container to the second collection position is adequate on the basis of the first collection position data, the second collection position data, the individual identification data, and data to indicate the predetermined transport amount.

In this way, the transport method is constructed such that it is confirmed in the transport confirming step whether or not the transport is adequate, on the basis of the individual identification data outputted in the sample container identifying step, the first collection position data outputted in the first judging step, the second collection position data outputted in the second judging step, and the data to indicate the predetermined transport amount to be used in the transport step. Accordingly, it is possible to avoid the sample misidentification, in the same manner as in the transport apparatus described above. Further, the technical concepts, which have been disclosed in relation to the transport apparatus described above, are also applicable equivalently to the transport method according to the present invention.

The present invention can be also grasped from an aspect of a transport program as follows. That is, the present invention resides in a transport program for transporting a sample as an analysis objective in a state of being accommodated in a sample container by means of a computer; wherein the transport program allows the computer to execute a sample container identifying step of performing individual identification of the sample container to output an identification result thereof as individual identification data; a first judging step of judging whether or not the sample container is positioned at a first collection position for collecting the sample from the sample container in order to perform a first analysis process to output a judgment result thereof as first collection position data; a transport step of transporting, from the first collection position to a second collection position, the sample container judged to be positioned at the first collection position in the first judging step by a predetermined transport amount calculated in accordance with the first collection position and the second collection position for collecting the sample from the sample container in order to perform a second analysis process; a second judging step of judging whether or not the sample container is positioned at the second collection position in relation to the sample container transported in the transport step to output a judgment result thereof as second collection position data; and a transport confirming step of confirming whether or not the transport of the sample container to the second collection position is adequate on the basis of the first collection position data, the second collection position data, the individual identification data, and data to indicate the predetermined transport amount.

In this way, the program is constructed such that it is confirmed in the transport confirming step whether or not the transport is adequate, on the basis of the individual identification data outputted in the sample container identifying step, the first collection position data outputted in the first judging step, the second collection position data outputted in the second judging step, and the data to indicate the predetermined transport amount to be used in the transport step. Accordingly, it is possible to avoid the sample misidentification, in the same manner as in the transport apparatus described above. Further, the technical concepts, which have been disclosed in relation to the transport apparatus described above, are also applicable equivalently to the transport method according to the present invention. Further, a recording medium, on which the foregoing program is recorded, also belongs to the category or scope of the present invention.

Further, the present invention can be also grasped from an aspect of a transport system. That is, the present invention resides in a transport system for transporting a sample as an analysis objective in a state of being accommodated in a sample container between a first analysis apparatus for performing a first predetermined analysis process and a second analysis apparatus for performing a second predetermined analysis process; the transport system comprising a first judging unit which judges whether or not the sample container is positioned at a first collection position for collecting the sample from the sample container for the first analysis apparatus and which outputs a judgment result thereof as first collection position data; a second judging unit which judges whether or not the sample container is positioned at a second collection position for collecting the sample from the sample container for the second analysis apparatus and which outputs a judgment result thereof as second collection position data; a container transport unit which successively transports the sample container including the sample accommodated therein to the first collection position and the second collection position; a sample container identification unit which performs individual identification of the sample container in a transport route for the sample container and which outputs an identification result thereof as individual identification data; and a transport confirming unit which confirms whether or not the transport of the sample container to the second collection position is adequate on the basis of the first collection position data, the second collection position data, the individual identification data, and data to indicate a predetermined transport amount calculated in accordance with the first collection position and the second collection position.

In this way, the transport system is constructed such that the transport confirming unit confirms whether or not the transport is adequate, on the basis of the individual identification data outputted by the sample container identification unit, the first collection position data outputted by the first judging unit, the second collection position data outputted by the second judging unit, and the data to indicate the predetermined transport amount to be used by the container transport unit. Accordingly, it is possible to avoid the sample misidentification, in the same manner as in the transport apparatus described above. Further, the technical concepts, which have been disclosed in relation to the transport apparatus described above, are also applicable equivalently to the transport system according to the present invention.

Effect of the Invention

When a series of analysis procedures including a plurality of analysis procedures are performed, then the sample misidentification can be reliably avoided, and the entire apparatus, which performs the series of analysis procedures, can be made compact.

BRIEF DESCRIPTION OF THE DRAWINGS

FIG. 6 shows a second drawing illustrating a schematic arrangement of a transport apparatus for transporting sample containers in the analysis system shown in FIG. 1.

MODE FOR CARRYING OUT THE INVENTION

The transport apparatus, the transport method, the transport program, and the transport system according to the mode for carrying out the present invention will be explained below with reference to the drawings. The following embodiments are constructed or arranged by way of example. The present invention is not limited to the construction or arrangements of the embodiments.

First Embodiment

Outline of Analysis System

Figure 1:
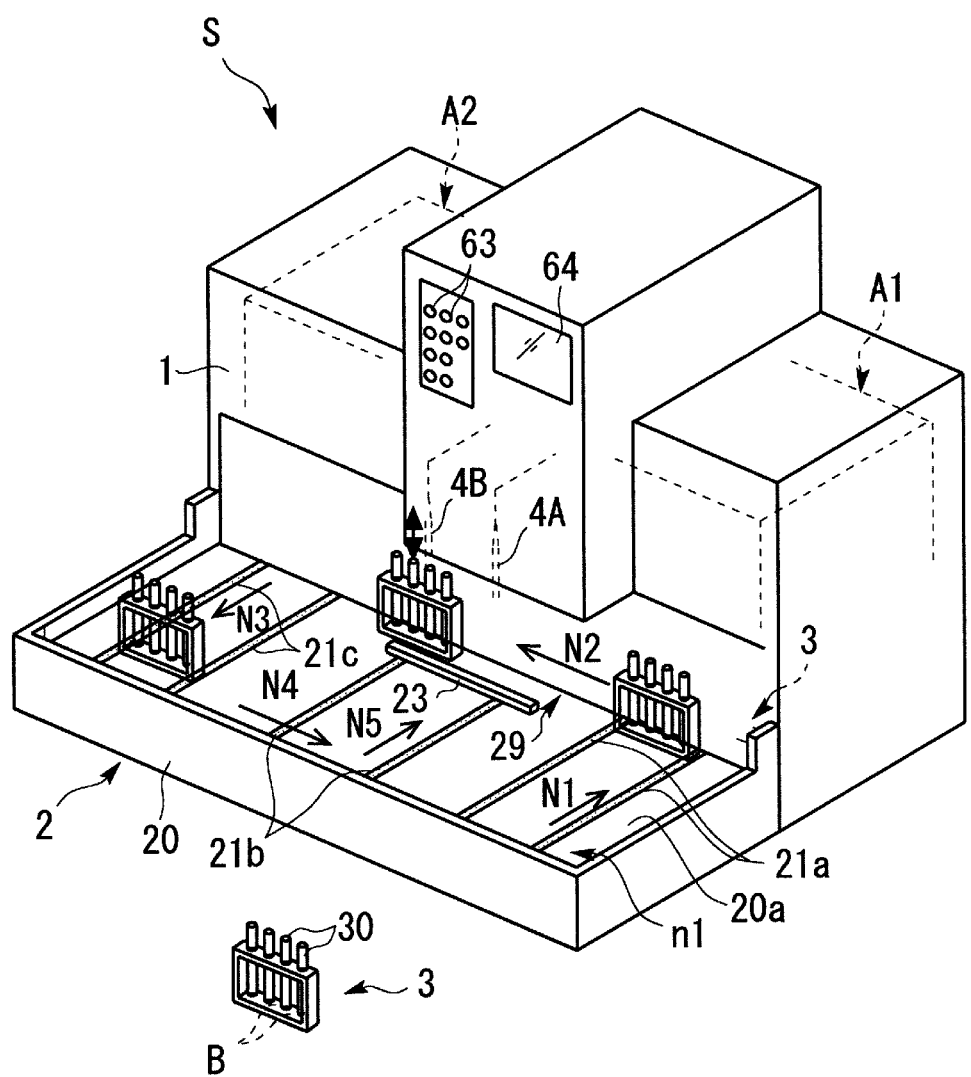
FIG. 1 shows a schematic arrangement of an analysis system including two analysis apparatuses for analyzing samples wherein a transport apparatus according to the present invention is applied to transport the samples between the analysis apparatuses.
Figure 2:
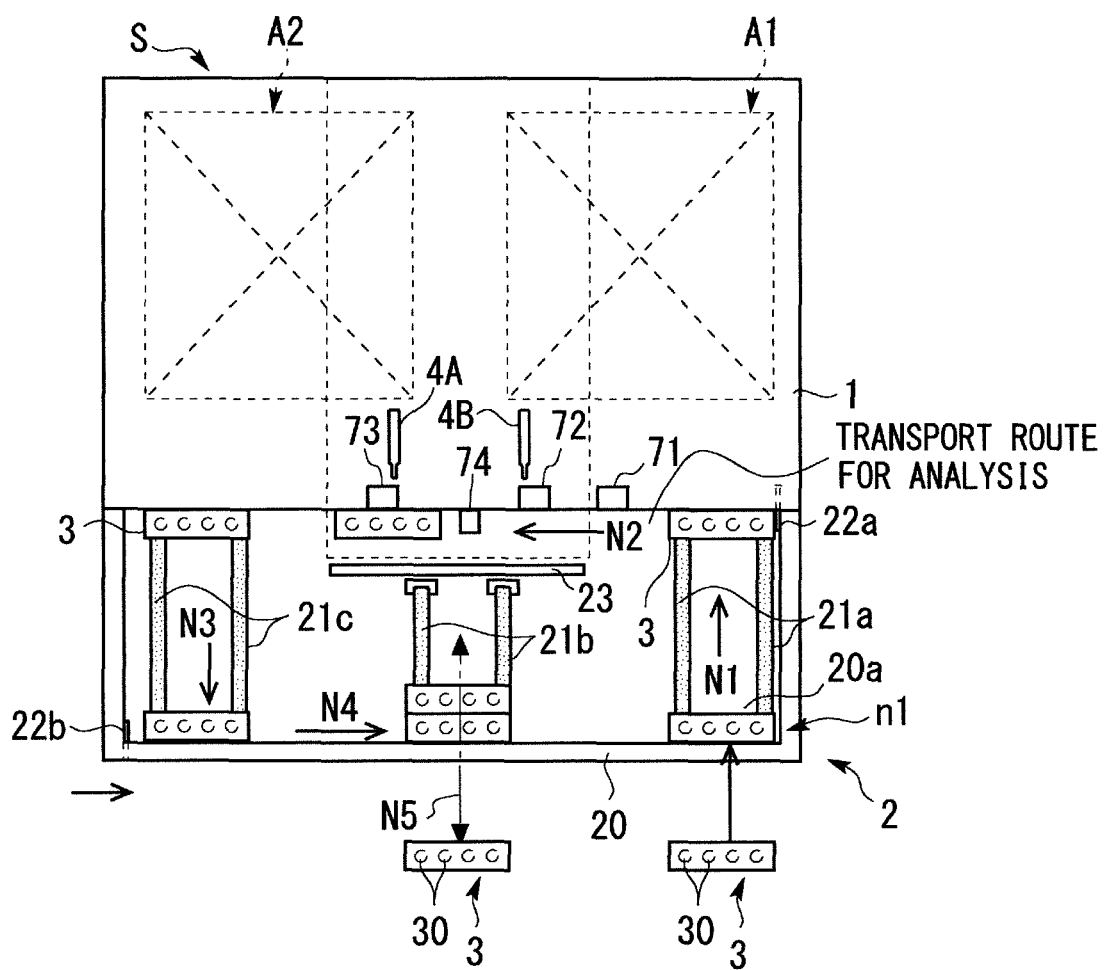
FIG. 2 shows a top view illustrating the analysis system shown in FIG. 1.
Figure 3:
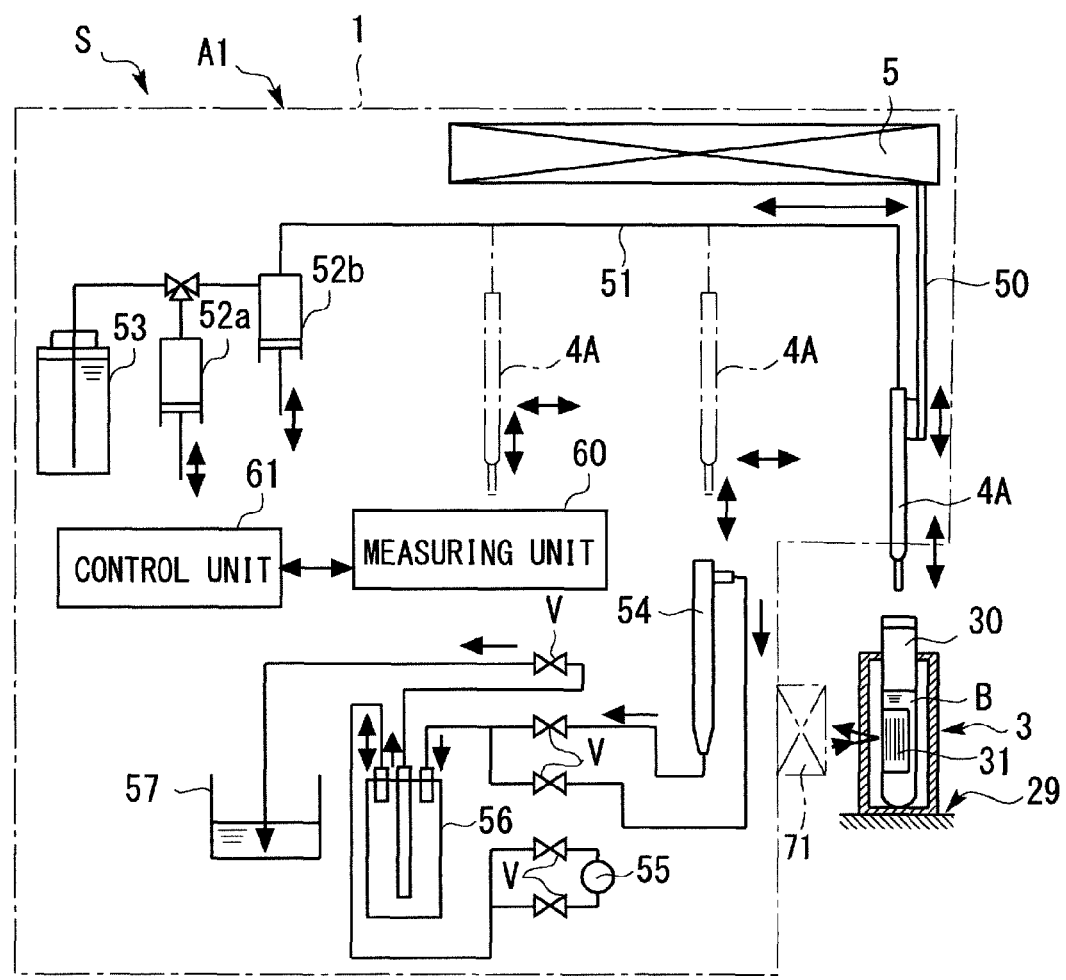
FIG. 3 schematically shows the operation state of constitutive components of the system upon the sample analysis in the analysis system shown in FIG. 1.

FIG. 1 shows a schematic arrangement of an analysis system S for performing predetermined analysis for samples, and FIG. 2 shows a top view illustrating the analysis system S. FIG. 3 shows the operation state of constitutive components of the system in relation to the sample collection for the purpose of analysis to be performed in the analysis system S. As shown in FIGS. 1 and 2, the analysis system S has first and second analysis apparatuses A1, A2 which are accommodated in one casing 1 and which are collected or aggregated into one unit, and a transport apparatus 2 which is provided to transport a plurality of urine sampling tubes (urine collection tubes) as sample containers between the analysis apparatuses in a state of being supported by sample racks 3.

The analysis system S is utilized in order that urines B as samples accommodated in the plurality of urine sampling tubes 30 are collected to analyze the components of the urines. The first analysis apparatus A1 and the second analysis apparatus A2 are apparatuses to perform the analysis processes relevant to the urines respectively. Specifically, the first analysis apparatus A1 performs the analysis process in relation to the urine qualitative analysis, and the second analysis apparatus A2 performs the analysis process in relation to the urinary sediment analysis.

The contents of the analysis processes performed by the analysis apparatuses A1, A2 described above are referred to by way of example. Any analysis apparatus, which performs the analysis process other than the above, is also applicable to the analysis system S. For example, the process may be performed for any analysis item in relation to urine other than the urine qualitative analysis and the urinary sediment analysis described above. Further, it is also possible to perform a variety of analysis processes in relation to blood. Therefore, the specified type of the sample analyzed by the analysis apparatuses A1, A2 and the specified contents of the analysis processes are not limited.

In this arrangement, as shown in FIG. 3, the first analysis apparatus A1 has a first nozzle 4A which is provided to suck and collect urine B from the urine sampling tube 30. The first nozzle 4A is supported by an arm 50 of a nozzle moving apparatus 5, and the first nozzle 4A is movable in the upward-downward direction.

The first analysis apparatus A1 can be basically constructed in the same manner as any conventionally known urine qualitative analysis apparatus. That is, the first analysis apparatus A1 is provided with syringe pumps 52$a$, 52$b$ which are connected to an upper portion of the first nozzle 4A via a tube 51, a cleaning solution tank 53, a washing vessel 54, a measuring unit 60, and a control unit 61. The syringe pumps 52$a$, 52$b$ perform such an operation that a cleaning solution (washing), which is stored in the cleaning solution tank 53, is fed into the first nozzle 4A via the tube 51 and such an operation that the negative pressure is generated in the first nozzle 4A in order to suck the sample. The washing vessel 54 is provided to wash or clean the first nozzle 4A. The first nozzle 4A is washed by feeding the cleaning solution into the first nozzle 4A via the tube 51 in a state in which the first nozzle 4A is allowed to advance into the washing vessel 54. The cleaning solution, which is supplied into the washing vessel 54, is supplied to a waste liquid tank 57 via an intermediate bottle 56 in accordance with the switching operation for a plurality of opening/closing valves V and an air pump 55.

The measuring unit 60 is provided with a spotting unit (not shown) in which urine B is sucked by the first nozzle 4A and urine B is discharged and spotted onto a test strip (test piece) installed in the measuring unit 60, and an instrument (not shown) with which the urine qualitative analysis is performed by using the test strip. Any conventional structure or arrangement, which makes it possible to perform the urine qualitative analysis, can be applied as the specified structure or arrangement. The control unit 61 is constructed by using a computer. The control unit 61 executes, for example, the process for calculating the glucose concentration from the measurement data obtained by the measuring unit 60 and the operation processes for the respective components of the first analysis apparatus A1.

As for the second analysis apparatus A2, any conventional structure or arrangement, which makes it possible to perform the urinary sediment analysis, can be applied as the specified structure or arrangement thereof. However, in this embodiment, a second nozzle 4B for sample collection, which is provided for the second analysis apparatus A2, is movable in only the upward-downward direction in the same manner as the first nozzle 4A, and the position for sample collection is unchangeable in the transport apparatus 2.

As shown in FIG. 3, an identification code 31 such as a bar code or the like is affixed to the urine sampling tube 30. The analysis system S is provided with a bar code reader 71 for reading the identification code 31. The individual identification data, which is read by the bar code reader 71, is the data to identify the individual of each of the urine sampling tubes. After the reading, the data is transmitted to the control unit 61 included in the analysis system S. The data is utilized as the reference data which is allowed to correlate with the data of the analysis process result of urine B in the first and second analysis apparatuses A1, A2. Further, as described later on, the individual identification data is also transmitted to a transport control unit 70 which is the control unit of the transport apparatus 2 that is in charge of the transport of the urine sampling tubes 30 between the analysis apparatuses A1, A2. The control unit 61 of the first analysis apparatus A1 shown in FIG. 3 can be commonly used to execute the operation control and various types of data processing in the second analysis apparatus A2 as well. Owing to this fact, it is also possible to adopt such an arrangement that the second analysis apparatus A2 is not provided with any inherent control unit.

Further, as shown in FIG. 1, a plurality of operation switches 63 and a display 64 for displaying the data are provided on outer surface portions of the casing 1 of the analysis system S. These components can be also commonly used for the first and second analysis apparatuses A1, A2 and for the transport apparatus 2.

<Arrangement of Transport Apparatus>

In this embodiment, the transport apparatus 2 transports the plurality of urine sampling tubes 30 from the first analysis apparatus A1 to the second analysis apparatus A2 in a state in which the plurality of urine sampling tubes 30 are retained upstandingly in the sample rack 3. Accordingly, it is possible to allow the sample to undergo the analysis processes performed by the respective analysis apparatuses. The transport apparatus 2 is provided with a frame 20 which is connected to a lower portion of the front surface of the casing 1, three sets of belts 21a to 21c which are capable of performing the circulating driving and which are positioned on an upper surface portion 20a of the frame 20, and two pushers 22a, 22b (see FIG. 2) which are movable in the horizontal direction. When the sample rack 3 is supplied to the position indicated by a symbol n1 in the transport apparatus 2, then the sample rack 3 is transported by the belts 21a in the direction of the arrow N1, and the sample rack 3 is thereafter transported by the pusher 22a in the direction of the arrow N2. As described later on, urine B, which is accommodated in the urine sampling tube 30, is collected into each of the analysis apparatuses during the process of movement in the direction of the arrow N2.

Subsequently, the sample rack 3 is transported by the belts 21c in the direction of the arrow N3, the sample rack 3 is thereafter transported by the pusher 22b in the direction of the arrow N4, and the sample rack 3 is supplied onto the belts 21b. The area, in which the belts 21b are provided, is the stock area for stocking the sample racks 3 for which the analysis processes have been completed. The sample rack 3, which is supplied to the stock area, is transported by the belts 21b in the direction of the arrow N5. However, owing to the presence of a stopper 23, any collision with the sample rack 3 transported in the direction of the arrow N2 is avoided. The stock area as described above, in which the belts 21b are provided, is provided by effectively utilizing the space formed between the belts 21a and the belts 21c. The transport apparatus 2 is not especially large-sized on account of the provision of the stock area.

Owing to the transport apparatus 2 which is constructed as described above and which is installed in the analysis system S, at first, the sample rack 3, which is introduced into the portion of the transport apparatus 2 indicated by the symbol n1, is successively transported along the route indicated by the arrows N1 to N5 as described above. In the process in which the sample rack 3 is transported in the direction of the arrow N2 on the transport route 29, the identification code 31 of each of the urine sampling tubes 30 is firstly read by the bar code reader 71. Subsequently, the first analysis apparatus A1 successively samples or collects urines B from the plurality of urine sampling tubes 30 by utilizing the first nozzle 4A, and the urine qualitative analysis is performed therefor. The second analysis apparatus A2 samples or collects urines B by utilizing the second nozzle 4B, and the urinary sediment analysis is performed therefor.

In this procedure, the following premise should be taken into consideration to analyze urine as the biological sample. That is, it is necessary to avoid the occurrence of the urine misidentification by all possible means when urine B is collected by the first analysis apparatus A1 and the second analysis apparatus A2, i.e., when urine as the analysis objective is analyzed. The transport apparatus 2 according to the present invention, which is carried on the analysis system S, is provided with the structure or arrangement to avoid the occurrence of the urine misidentification as described above. Further, the sample transport control, in which the urine misidentification is avoided, is executed by utilizing the structure or arrangement. In this context, the structure or arrangement of the transport apparatus 2 will be explained in detail on the basis of FIGS. 2 and 4, and the concerning transport control will be explained on the basis of FIG. 5.

Figure 4:
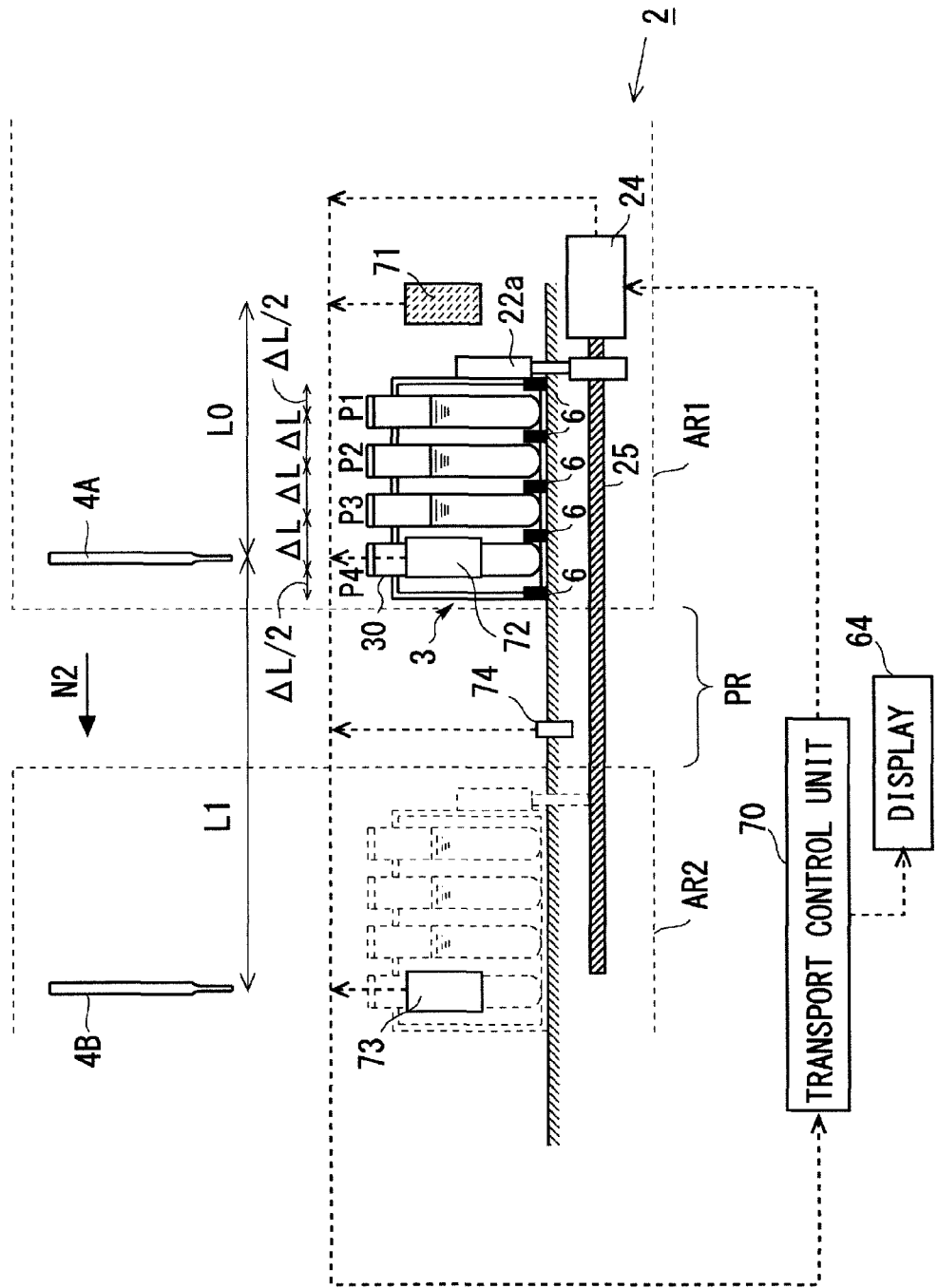
FIG. 4 shows a first drawing illustrating a schematic arrangement of the transport apparatus for transporting sample containers in the analysis system shown in FIG. 1.

As shown in FIGS. 2 and 4, the transport apparatus 2 is constructed such that the pusher 22a forms the contact state with respect to the sample rack 3 which supports the plurality of urine sampling tubes 30, and the sample rack 3 is transported in the direction of the arrow N2 by means of the pressing force exerted from the pusher 22a. The pusher 22a is connected to a driving screw 25 connected to an output shaft of a driving motor 24 installed at a lower surface portion of the frame 20 (positioned on the back side of an upper surface portion 20a in relation to FIG. 2). When the driving motor 24 is driven, the pusher 22a can be moved in the direction of the arrow N2 or in the opposite direction opposite thereto. Therefore, the direction of the arrow N2 corresponds to the transport direction of the sample rack 3 to make it possible to collect urine by each of the analysis apparatuses. The route, in which the sample rack 3 is transported along with the concerning direction, is referred to as "transport route for analysis".

In this arrangement, the plurality of urine sampling tubes 30 can be supported in the sample rack 3. In a state shown in FIG. 4, the four urine sampling tubes 30 are arranged in the sample rack 3 in one array in the transport direction so that the spacing distance between the urine sampling tubes 30 is a constant distance of ΔL. In this arrangement, the positions, at which the respective urine sampling tubes are supported, are designated as P4, P3, P2, P1 successively in this order as starting from the frontward position in the transport direction. As shown in FIG. 4, the distance is ΔL/2 between the urine sampling tube 30 positioned on each of the left and right end sides and the end portion of the sample rack 3 disposed in the vicinity thereof. Therefore, the length of the sample rack 3 in the transport direction is 4L. Further, rib portions 6 are provided at equal intervals (equal spacing distances) between the urine sampling tubes 30 disposed adjacently to the left and right end portions of the sample rack 3, at positions of the lower portion of the sample rack 3 opposed to the floor surface of the transport route for analysis. As appreciated from FIG. 4 as well, the spacing distance between the adjoining rib portions 6 is ΔL which is the same as the spacing distance between the urine sampling tubes 30.

With reference to FIG. 4, the area, which is spatially occupied by the analysis apparatus A1 along with the transport of the sample rack 3 in the direction of the arrow N2, is designated as AR1, and the area, which is spatially occupied by the analysis apparatus A2, is designated as AR2. Therefore, the sample rack 3 is transported from the side of the area AR1 to the side of the area AR2. However, a passage area PR, through which the sample rack 3 passes, is formed between the area AR1 and the area AR2. A passage sensor 74, which detects the passage amount of the sample rack 3, is provided on the transport route for analysis belonging to the passage area PR. The passage sensor 74 has a protruding portion which slightly protrudes on the floor surface of the transport route for analysis. The protruding portion makes contact with the rib portion 6 of the sample rack 3 to be transported, and thus the protruding portion is pushed and depressed into the floor of the transport route for analysis in this arrangement. Further, in the floor of the transport route for analysis, the movement of the depressed protruding portion is optically sensed or detected by utilizing a photodiode. Thus, it is possible to electrically sense or detect the passage of the rib portion 6 of the sample rack 3. When the sample rack is further transported after the contact of the rib portion 6 with the protruding portion, and the rib portion 6 and the protruding portion are released from the contact state, then the state is brought about again such that the protruding portion protrudes on the floor surface of the transport route for analysis by means of the urging force brought about by a spring or a counter weight so that the protruding portion is ready for the next contact with the rib portion 6. Therefore, the passage sensor 74 can sense or detect the passage amount of the sample rack 3 by using the unit of the spacing distance $\Delta L$ between the rib portions 6.

In this arrangement, the transport apparatus 2 is provided with a transport control unit 70 which is provided to electrically control the transport of the sample rack 3. The transport control unit 70 corresponds to a computer. The transport control is realized by a computer program executed on the concerning computer including, for example, unillustrated CPU, memory, and hard disk. The input of the operation instruction into the transport apparatus 2 can be performed by utilizing the operation switches 63 provided for the analysis system S. The bar code reader 71 is installed on the most upstream side of the transport route for analysis. As described above, the bar code reader 71 performs the individual identification of each of the urine sampling tubes 30 supported by the sample rack 3. The identification result thereof is transmitted as the individual identification data to the transport control unit 70.

A first position confirming sensor 72, which is provided to confirm the presence of the urine sampling tube 30 supported by the sample rack 3, is installed at a position corresponding to the collection position for collecting urine by the first nozzle 4A (hereinafter referred to as "first collection position") on the downstream side from the bar code reader 71 in the transport route for analysis. The first position confirming sensor 72 is a sensor for optically sensing or detecting whether or not the urine sampling tube for accommodating urine B as the collection objective is positioned at the first collection position in the area AR1. The detecting light, which is emitted from a light-emitting portion, is reflected by the urine sampling tube 30, and the reflected light therefrom is sensed or detected by a light-receiving portion. Accordingly, the presence of the urine sampling tube at the first collection position is detected. Owing to the relatively simple arrangement in which the detecting light is emitted and the reflected light is received, the first confirming sensor 72 is compact as compared with the bar code reader 71, and the cost can be suppressed to be low as well. This feature is the same as or equivalent to that of a second position confirming sensor described later on. The result of detection performed by the first position confirming sensor 72 is electrically transmitted as the first collection position data to the transport control unit 70.

Further, the second position confirming sensor 73, which is provided to confirm the presence of the urine sampling tube 30 supported by the sample rack 3, is installed at a position corresponding to the collection position for collecting urine by the second nozzle 4B (hereinafter referred to as "second collection position") on the downstream side from the first position confirming sensor 72 in the transport route for analysis. The second position confirming sensor 73 is a sensor for optically detecting whether or not the urine sampling tube 30 for accommodating urine B as the collection objective is positioned at the second collection position in the area AR2, in the same manner as the first position confirming sensor 72. The result of detection performed by the second position confirming sensor 73 is electrically transmitted as the second collection position data to the transport control unit 70.

The driving motor 24 is provided with an encoder which is capable of detecting the rotation state thereof. The rotational position information of the output shaft of the driving motor 24 is transmitted from the encoder to the transport control unit 70. Accordingly, the transport control unit 70 can grasp the position of the pusher 22a in the transport route for analysis.

Figure 5:
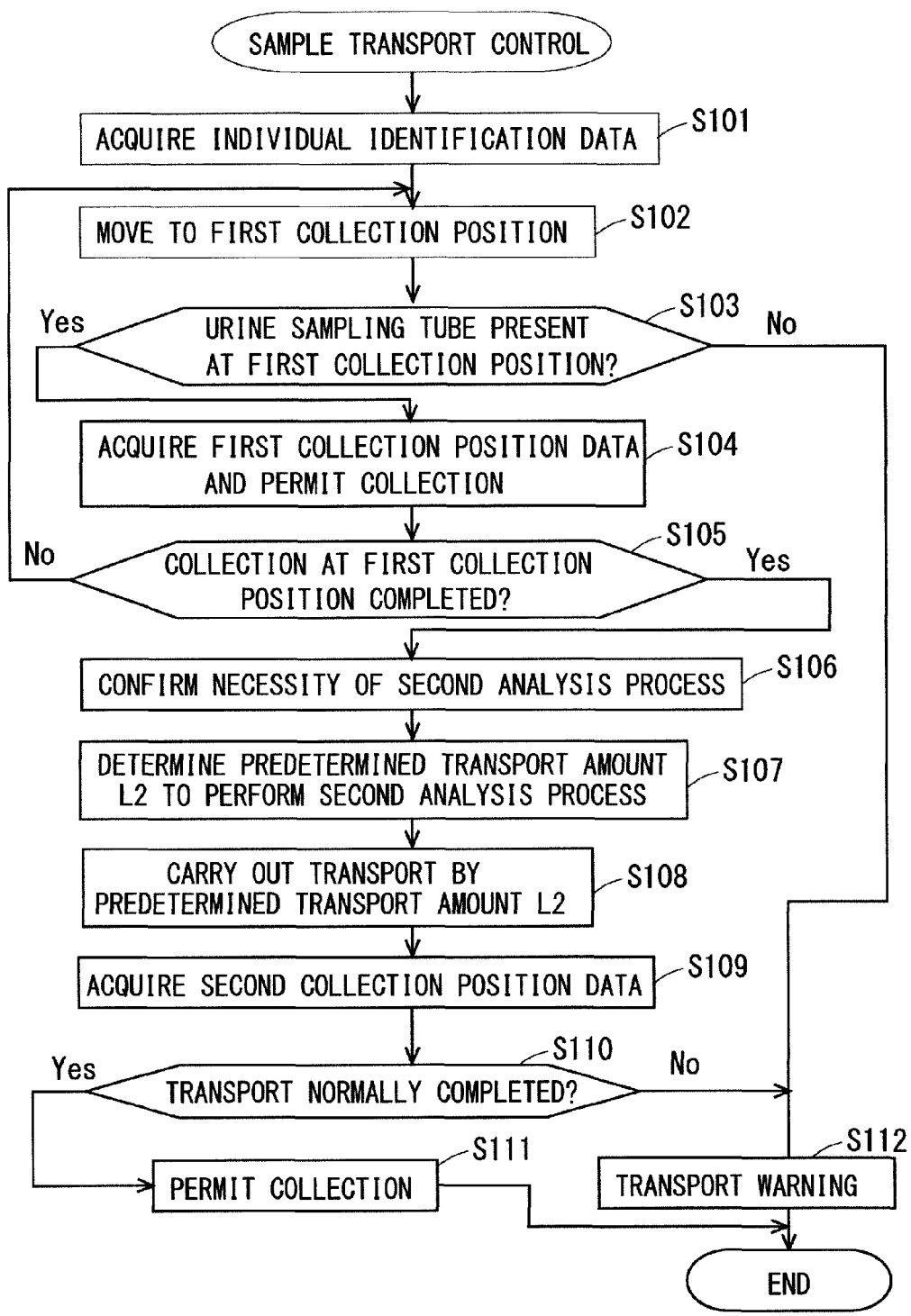
FIG. 5 shows a flow chart of the control to transport the sample as executed in the transport apparatus shown in FIG. 4.

In the case of the transport apparatus 2 shown in FIG. 4, the distance between the first collection position at which urine B is collected by the first nozzle 4A and the second collection position at which urine is collected by the second nozzle 4B is fixedly set to the distance L1. The transport amount (hereinafter referred to as "predetermined transport amount") by which the transport is performed by the transport apparatus 2 from the side of the first collection position to the side of the second collection position, i.e., the predetermined transport amount by which the sample rack 3 is moved by being pushed by the pusher 22a is determined on the basis of the distance L1. Details thereof will be described later on. An explanation will now be made on the basis of FIG. 5 about the transport control in relation to the transport of the sample rack 3 performed by the transport apparatus 2. The sample transport control shown in FIG. 5 is a series of transport processes realized by executing the program recorded in the memory included in the transport control unit 7 which serves as the computer as well. Specifically, the concerning transport control is executed when the sample rack 3 is carried by the belts 21a in the direction of the arrow N1 and an unillustrated sensor detects the arrival at the transport route for analysis.

At first, in S101, the individual identification data is acquired for each of the urine sampling tubes 30 detected by the bar code reader 71. Specifically, when the sample rack 3, which is pushed from the backward position in the transport direction by the aid of the contact state with respect to the pusher 22a, passes in front of the bar code reader 71, the individual identification data is acquired for each of the urine sampling tubes supported thereby. Accordingly, the transport control unit 70 can know the number of the urine sampling tubes 30 supported by the sample rack 3 and the arrangement of the urine sampling tubes 30 in the sample rack 3. In the state shown in FIG. 4, the four urine sampling tubes 30 are arranged in one array in the sample rack 30. When the process in S101 is completed, the routine proceeds to S102.

In S102, the sample rack 3 is moved to the first collection position at which urine B is collected by the first nozzle 4A. As described above, as for the first analysis apparatus A1, urines B accommodated in all of the urine sampling tubes 30 are collection objectives. Accordingly, the sample rack 3 is pushed by the pusher 22a by the distance for which the arrangement of the urine sampling tubes 30 in the sample rack 3 is taken into consideration with respect to the distance L0 between the bar code reader 71 and the first collection position known beforehand. Accordingly, the urine sampling tube 30 (urine sampling tube 30 disposed at the position P4 shown in FIG. 4), from which the collection is to be firstly performed by the first nozzle 4A, is moved to the first collection position. The following urine sampling tubes 30 disposed thereafter are successively pushed by the pusher 22a by the amount corresponding to the distance ($\Delta L$) between the adjoining urine sampling tubes while considering the arrangement of the urine sampling tubes 30 in the sample rack 3. In the example shown in FIG. 4, when the individual identification is performed for the urine sampling tube 30 disposed at the position P1 at which the individual identification is performed at last, the sample rack is pushed by the aid of the pusher 22a by the distance which is obtained by subtracting, from the distance L0, the distance $3\Delta L$ between the urine sampling tube 30 at the position P1 and the urine sampling tube at the head position P4. Accordingly, the urine sampling tube 30 at the position P4 is theoretically positioned at the first collection position. After that, the sample rack 3 is successively pushed by $\Delta L$, and thus the position of each of the urine sampling tubes at the position P3 and the followings is adjusted to arrive at the first collection position. When the process in S102 is completed, the routine proceeds to S103.

In S103, it is judged whether or not the urine sampling tube 30 is present at the first collection position, on the basis of the detection result obtained by the first position confirming sensor 72 described above. If the affirmative judgment is made in this step, then the routine proceeds to S104, and thus the first collection position data, which means that "urine sampling tube 30 as the collection objective is present at the first collection position", is outputted from the first position confirming sensor 72. The first collection position data is acquired by the transport control unit 70. Further, the urine collection from the urine sampling tube 30 is permitted for the first nozzle 4A, and urine is subjected to the analysis process performed in the first analysis apparatus A1. On the other hand, if the negative judgment is made in S103, it is meant that the urine sampling tube, which should be theoretically present at the first collection position ordinarily or originally, is not present at the first collection position. Therefore, the first collection position data, which means that "urine sampling tube 30 as the collection objective is not present at the first collection position", is outputted from the first position confirming sensor 72 to the transport control unit 70. Accordingly, it is judged by the transport control unit 70 that the sample rack 3 is not transported normally to the first collection position for any reason. A warning is given with respect to the transport (process in S111). The transport warning may be displayed on the display 64 of the analysis system S, and/or the transport warning may be given by voice from an unillustrated speaker. Simultaneously with the transport warning, the driving motor 24 is stopped, and the transport of the sample rack 3 is stopped. Accordingly, the misidentification of urine, which would be otherwise caused by the abnormal transport, is avoided beforehand.

In this procedure, if the process in S104 is completed, and the collection of urine by the first nozzle 4A is completed, then it is judged in S105 whether or not the collection of urine is completed at the first collection position. If the affirmative judgment is made in the concerning judgment, the routine proceeds to S106. If the negative judgment is made, the processes in S102 and followings are successively repeated. In this embodiment, the relative positional relationship between the sample rack 3 and the first nozzle 4A, which is provided when the affirmative judgment is made in the judgment in S105, resides in such a state that the urine sampling tube 30 at the position P1 is positioned just under the first nozzle 4A.

As described above, the second analysis process, which is performed by the second analysis apparatus A2, is performed for only samples (urines) judged to fulfill a certain condition on the basis of the results of the first analysis process, unlike the first analysis process which is carried out for all of urines. Accordingly, in S106, it is confirmed whether or not the second analysis process is required, taking the result of the first analysis process into consideration. In this embodiment, the following explanation will be made assuming that only urine B, which is accommodated in the urine sampling tube 30 at the position P4 of the four urine sampling tubes aligned in the sample rack 3, is the objective of the second analysis process. If it is judged in S106 that it is unnecessary to perform the second analysis process for any one of urines, then it is unnecessary to feed the sample rack 3 to the second analysis apparatus, and hence this control is completed. In this case, the sample rack 3 is not subjected to the analysis process to be performed by the second analysis apparatus A2. The sample rack 3 successively undergoes the belts 21c, the pusher 22b, and the belts 21b, and the sample rack 3 is stocked in the stock area.

Subsequently, in S107, the predetermined transport amount L2 is determined, which is necessary to perform the transport from the area AR1 of the first analysis apparatus A1 to the area AR2 of the second analysis apparatus A2 in order to perform the second analysis process. In this embodiment, the distance between the first nozzle 4A and the second nozzle 4B is L1, and only the urine sampling tube 30 at the position P4, for which the first analysis process has been firstly performed, is the objective of the second analysis process. Therefore, the urine sampling tube 30 at the position P1 is positioned just under the first nozzle 4A at the point in time at which the first analysis process is completed (at the point in time at which the affirmative judgment is made in S105). Taking this fact into consideration, the predetermined transport amount L2 is determined to be (L1-$3\Delta L$). In another example, if the objective of the second analysis process is not the urine sampling tube 30 at the position P4 but the objective of the second analysis process is only the urine sampling tube 30 at the rearmost position P1, then the final objective of the first analysis process is the urine sampling tube 30 at the position P1, and the first objective of the second analysis process is also the urine sampling tube 30 at the position P1. Therefore, the predetermined transport amount L2 is L1. The sample rack 3 is pushed by the aid of the contact state with respect to the pusher 22a by the amount of the predetermined transport amount determined in S107, and the transport is carried out to the second analysis apparatus A2 (process in S108).

If the process in S108 is completed, the routine proceeds to S109. In S109, the second collection position data is acquired by the second position confirming sensor 73. Specifically, if the presence of the urine sampling tube is confirmed by the second position confirming sensor 73 after the process in S108, then the second collection position data, which means that "urine sampling tube 30 as the collection objective is present at the second collection position", is outputted from the second position confirming sensor, and the data is acquired by the transport control unit 70. On the contrary, if the presence of the urine sampling tube is not confirmed by the second position confirming sensor 73 after the process in S108, then the second collection position data, which means that "urine sampling tube 30 as the collection objective is not present at the second collection position", is outputted from the second position confirming sensor, and the data is acquired by the transport control unit 70. If the process in S109 is completed, the routine proceeds to S110.

In S110, it is judged whether or not the transport of the sample rack 3 to the second analysis apparatus A2 is normally performed, taking the contents of the second collection position data acquired in S109 into consideration. That is, if the contents of the second collection position data mean that "urine sampling tube 30 as the collection objective is present at the second collection position", then it is judged that the concerning transport is normally performed, and it is permitted to collect urine B by means of the second nozzle 4B (process in S111). On the other hand, if the contents of the second collection position data mean that "urine sampling tube 30 as the collection objective is not present at the second collection position", then it is judged that the concerning transport is not normally performed, and the process of transport warning is performed in S112.

The judgment in S110 practically resides in a process to judge whether or not the transport to the second analysis apparatus A2 is adequate on the basis of the first collection position data, the second collection position data, the individual identification data, and the data to indicate the predetermined transport amount, in accordance with the execution of the processes of S103 to S109. When the process as described above is performed by utilizing the position confirming sensor which is compact and which is provided at the low cost as described above, then the transport apparatus 2 itself can be constructed to be compact, and it is possible to correctly judge whether or not the transport of the sample rack 3 between the analysis apparatuses is adequate. Therefore, it is possible to avoid the misidentification of urine.

It is also appropriate to judge whether or not the transport is adequate, by further considering the contact state between the pusher 22a and the sample rack 3 in the judgment in S110. That is, in the transport apparatus 2, the pusher 22a is brought in contact with the sample rack 3 from the backward position in the transport direction, and the transport is performed by pushing the same. Taking this fact into consideration, if the contact state disappears for any reason, it is impossible to completely negate such a possibility that the transport of the sample rack 3 is not performed normally. In view of the above, the process to confirm the concerning contact state is performed. Further, if it is judged that the contact state disappears as a result thereof, it is also appropriate to judge that the transport is not performed normally, irrelevant to the contents of the second collection position data so that the process of transport warning in S112 is performed. In other words, even if the contents of the second collection position data mean that "urine sampling tube 30 as the collection objective is present at the second collection position", then the priority is given to the judgment that the contact state disappears during the process of transport, and it is judged that the normal transport is not performed. When the process as described above is performed, it is possible to avoid the misidentification of urine more reliably.

In this procedure, the confirmation of the normal contact state between the pusher 22a and the sample rack 3 can be realized, for example, by the following method.
(Method 1)

The contact state is confirmed on the basis of the movement amount of the pusher 22a obtained from the encoder of the driving motor 24. Specifically, if the presence of any urine sampling tube 30 is confirmed by the second position confirming sensor 73 although the movement amount of the pusher 22a is less than the predetermined transport amount L2, it is rationally considered that the sample rack 3 is moved by any external factor other than the pusher 22a (for example, any contact of a person who performs the operation of the analysis system S). Therefore, in the situation as described above, it is judged that the normal contact state between the pusher 22a and the sample rack 3 disappears.
(Method 2)

The contact state is confirmed by considering the movement amount of the sample rack 3 detected by the passage sensor 74 as well, in addition to the movement amount of the pusher 22a obtained from the encoder of the driving motor 24. Specifically, if the movement amount of the pusher 22a is different from the passage amount of the sample rack 3, it is rationally considered that the sample rack 3 is moved by any external factor other than the pusher 22a (for example, any contact of a person who performs the operation of the analysis system S). Therefore, in the situation as described above, it is judged that the normal contact state between the pusher 22a and the sample rack 3 disappears. The movement amount of the sample rack 3 may be detected by utilizing a reflection type optical sensor in place of the passage sensor 74.
(Method 3)

The change of the load concerning the driving motor 24 is detected from the driving current of the driving motor 24. If the driving current is suddenly decreased, it is judged that the normal contact state between the pusher 22a and the sample rack 3 disappears, for the following reason. That is, it is considered that the load concerning the driving motor 24 is suddenly decreased when the contact state disappears.

It is enough that each of the first and second nozzles referred to in the present invention has the function to collect the sample from the sample container. For example, each of the first and second nozzles may have a simple tube-shaped form composed of, for example, rubber or resin.

Modified Embodiment

In the embodiment described above, the positions of the both nozzles for collecting urine are fixed. However, at least any one of the nozzles may be constructed so that the position is changeable in the transport direction during the analysis. A specified arrangement, in which the position is changeable, can be realized by using any appropriate driving means including, for example, an actuator such as a reciprocating cylinder or the like, and a circulating driving belt. In this embodiment, an example is shown as follows, in which the position of the nozzle is changeable. That is, the collection position of the second nozzle 4B (second collection position) is fixed to a predetermined position on the transport route for analysis in the same manner as in the embodiment described above, while the collection position of the first nozzle 4A (first collection position) is changeable in the transport direction N2 and the direction opposite thereto on the upstream side of the transport route for analysis from the second nozzle 4B.

An explanation will be made more specifically on the basis of FIG. 4. The collection position of the first nozzle 4A is changeable so that the urine sampling tubes 30 existing at the respective positions P1 to P3 can be also accessed, while using the position of P4 as the reference position in the same manner as in the foregoing embodiment. One of the objects of the change of the collection position of the first nozzle 4A from the reference position (P4) is exemplified to avoid such a situation that the driving of the pusher 22a of the transport apparatus 2 is stopped for not less than a certain period of time due to the stagnation or stop of the analysis process performed by the second analysis apparatus A2 and the efficiency of the entire process of the analysis system S is lowered.

When the analysis processes as described above are executed by the respective analysis apparatuses, the analysis process is stopped for not less than a certain period of time in the second analysis apparatus A2, for example, during a period in which the second nozzle 4B is washed for a relatively long period of time. If such a situation arises, a waiting state, in which the pusher 22a stops the transport of the sample rack 3, is set in accordance with the control performed by the control unit 61.

If such a waiting state is set, then the sample collection position of the first nozzle 4A, i.e., the first collection position is moved in the direction opposite to the sample rack transport direction N2 as shown in FIG. 4, and thus the first collection position is successively changed from the position P4 to the position P1. Urine B, which has not been subjected to the analysis process yet, is collected by the first nozzle 4A, and the analysis process is performed therefor. The timing, at which the sample collection position of the first nozzle 4A is returned to the reference position P4, is appropriately provided, for example, after the completion of the urine collection at the final position P1. However, there is no limitation thereto.

When the position of the first nozzle 4A is changeable as described above, then the first analysis apparatus A1 can be operated efficiently, and it is possible to shorten the period of time of such a state that the operations of both of the first and second analysis apparatuses A1, A2 are stopped, even in the case of such a situation that it is difficult to transport the urine sampling tube 30 due to the stagnation or stop of the process performed by the second analysis apparatus A2. Owing to this fact, it is possible to enhance the analysis process efficiency of the entire analysis system S.

When the sample collection position of the first nozzle 4A (first collection position) is changeable as described above, it is necessary that the first position confirming sensor 72 should be provided corresponding to the first collection position subjected to the position change, in order to execute the sample transport control shown in FIG. 5. For example, position confirming sensors, which correspond to the positions P3 to P1 respectively, may be provided in addition to the first position confirming sensor 72 corresponding to the reference position P4. When the concerning sample transport control is executed, the processes in S103, S104 of the concerning sample transport control may be performed in relation to the position confirming sensor (hereinafter referred to as "corresponding position confirming sensor") corresponding to the first collection position subjected to the position change. When the predetermined transport amount L2 is determined in S108, it is also appropriate to reflect the distance between the corresponding position confirming sensor and the first position confirming sensor 72 corresponding to the reference position P4.

Alternatively, it is also appropriate to adopt such an arrangement that the position of the first position confirming sensor 72 is also changed in synchronization with the change of the first collection position, in place of the installation of the position confirming sensors at the positions P4 to P1 respectively. Also in this case, it is preferable that the process contents of S103, S104, S108 are changed in the same manner as in the foregoing case.

In the embodiment described above, the sample collection position of the first nozzle 4A (first collection position) is changeable. However, in place thereof, the sample collection position of the second nozzle 4B (second collection position) may be changeable, or both of the collection positions may be changeable. Also in these cases, as for the sample transport control shown in FIG. 5, the concerning control can be carried out by installing the position confirming sensor corresponding to the collection position subjected to the position change, and/or appropriately correcting the process of, for example, S103 as described above.

In the present invention, when the sample is collected while changing the sample collection position of one of the first and second nozzles during the period in which the transport apparatus is in the predetermined waiting state, the sample, which has not been collected yet, is basically collected. However, there is no limitation thereto. For example, when the first and second analysis apparatuses A1, A2 are operated, the collection of urine B from the identical urine sampling tube 30 and the analysis process therefor are repeatedly executed a plurality of times in some cases. In such a situation, when the urine is collected while changing the collection position of the nozzle during the period in which the transport apparatus 2 is in the predetermined waiting state, the collection for the second time and the followings may be performed from the urine sampling tube for which the urine collection for the first time has been already completed. The mode, in which the operation is performed as described above, is also included in the technical scope of the present invention.

Second Embodiment

FIG. 6 shows a third embodiment of a transport apparatus 2 according to the present invention. In the embodiment shown in FIG. 6, the first analysis apparatus A1 and the second analysis apparatus A2 are analysis apparatuses in relation to urine in the same manner as in the first embodiment. In the transport apparatus 2 according to this embodiment, as shown in FIG. 6, the two sample racks 3, which are connected to one another, can be transported along the transport route for analysis. In particular, the distance between the first collection position and the second collection position is set to L3 which is longer than L1 provided in the first embodiment, wherein the length of the passage area PR is secured to be relatively long. The concerning sample rack 3 is transported such that the pusher 22a makes contact from the backward position of the sample rack 3 to allow the pressing force to act thereon, in the same manner as in the first embodiment. In this arrangement, when another sample rack 3' (having the same size and the same shape as those of the sample rack 3) is present in front of the concerning sample rack 3 in the transport direction, then the sample rack 3 is brought in contact with the sample rack 3', and the connection state between the sample rack 3 and the sample rack 3' is formed by the aid of the contact state therebetween. Therefore, the connection state, which is referred to herein, does not mean the attainment of such a state that the sample rack 3 and the sample rack 3' are strongly connected to one another so that they are not separated from each other, but the connection state means the attainment of such a state that the pressing force applied from the pusher 22a can be transmitted by the aid of the contact state in the same manner as in the relationship between the pusher 22a and the sample rack 3. In this way, the plurality of sample racks are connected to one another and they are transported by the pusher 22a. Thus, it is possible to efficiently supply urine to the respective analysis apparatuses.

In the mode shown in FIG. 6, the contact portions are formed at the two places between the pusher 22a and the sample rack 3 and between the sample rack 3 and the sample rack 3'. Therefore, it is feared that the contact state may disappear at these portions on account of any factor, and it becomes impossible to perform the normal transport. However, even when the sample racks are transported in such a mode, it is possible to reliably avoid the sample misidentification during the transport by applying the sample transport control shown in FIG. 5 in principle. As described above, it is possible to secure the relatively long length of the passage area PR. Therefore, the size of the analysis system S itself is slightly increased, but the entire apparatus for performing the series of analysis procedures can be made compact in the same manner as in the other embodiments as compared with the conventional technique.

Further, in order to more appropriately judge whether or not the transport of the sample rack 3 is adequate, it is also allowable to utilize the deviation or discrepancy of the passage amount between the sample rack 3 and the sample rack 3' in the passage area PR. Specifically, it is judged whether or not the transport is adequate on the basis of the passage amount detected by the passage sensor 74 when the transport is performed by the pressing force applied from the pusher 22a after the sample rack 3 and the sample rack 3' are connected to one another.

In this embodiment, two passage sensors 74 are arranged in the passage area PR while providing a spacing distance longer than the length 4ΔL of one sample rack 3. Accordingly, the passage amount of the sample rack 3' can be detected by one passage sensor 74, and the passage amount of the sample rack 3 can be simultaneously detected by another passage sensor 74. In this arrangement, if any deviation arises between the passage amounts outputted from the both sensors, it is possible to judge that the sample rack 3 and the sample rack 3' are not transported while being pressed by the pusher 22a by the aid of the contact state between the both for any reason. In such a situation, it is feared that the normal transport of the sample rack is not realized. Therefore, when the sample transport control shown in FIG. 5 is executed, it is judged that the transport is not normally completed irrelevant to the contents of the second collection position data in the process in S110. Accordingly, the safe sample transport is secured.

As for the means for confirming the connection state between the sample rack 3 and the sample rack 3', it is also appropriate to perform the detection by providing an optical sensor like the position confirming sensor at a predetermined position at which the both racks are brought in contact with each other. Alternatively, the connection state as described above may be confirmed by detecting the increase in the load brought about by the contact of the sample rack 3 with the sample rack 3' on the basis of the increase in the driving current concerning the driving motor 24.

Third Embodiment

Other Embodiments

As described above, the present invention includes a computer program for performing the sample transport control in an embodiment thereof. Further, a medium, on which the concerning program is stored (recorded) on the recording medium capable of being read by the computer, also belongs to the category or scope of the present invention. As for the recording medium on which the concerning program is stored (recorded), it is possible to judge whether or not the transport based on the sample transport control described above is adequate, by allowing the computer to read the program on the recording medium so that the program is executed.

The recording medium, which is capable of being read by the computer, herein refers to such a recording medium that the information, which includes, for example, the data and the programs, can be accumulated in accordance with the electrical, magnetic, optical, mechanical, or chemical function, and the information can be read from the computer. Among the recording media as described above, those removable from the computer include, for example, floppy (trade name) disk, magneto-optical disk, CD-ROM, CD-R/W, DVD, Blu-ray Disc, DAT, 8 mm tape, and memory card. The recording media fixed to the computer include, for example, hard disk and ROM (read only memory).

PARTS LIST

1: casing, 2: transport apparatus, 3, 3': sample rack, 4A: first nozzle, 4B: second nozzle, 22a, 22b: pusher, 24: driving motor, 30: urine sampling tube, 63: operation switch, 64: display, 70: transport control unit, 71: bar code reader, 72: first position confirming sensor, 73: second position confirming sensor, 74: passage sensor, A1: first analysis apparatus, A2: second analysis apparatus, PR: passage area.

The invention claimed is:

1. A transport apparatus for transporting a sample as an analysis objective in a state of being accommodated in a sample container, the transport apparatus comprising:
   a first judging unit which judges whether or not the sample container is positioned at a first collection position for collecting the sample from the sample container in order to perform a first analysis process and which outputs a judgment result thereof as first collection position data;
   a second judging unit which judges whether or not the sample container is positioned at a second collection position for collecting the sample from the sample container in order to perform a second analysis process and which outputs a judgment result thereof as second collection position data;
   a container transport unit which successively transports the sample container to the first collection position and the second collection position;
   a sample container identification unit which performs individual identification of the sample container in a transport route for the sample container and which outputs an identification result thereof as individual identification data; and
   a transport confirming unit which confirms whether or not the transport of the sample container to the second collection position is adequate on the basis of the first collection position data, the second collection position data, the individual identification data, and data to indicate a predetermined transport amount calculated in accordance with the first collection position and the second collection position.

2. The transport apparatus according to claim 1, wherein the sample container identification unit is provided on an upstream side from the first collection position in the transport route for the sample container.

3. The transport apparatus according to claim 1, wherein the container transport unit transmits a force to successively transport the sample container to the first collection position and the second collection position via a contact portion formed between the container transport unit and the sample container.

4. The transport apparatus according to claim 1, wherein the transport confirming unit judges that the sample container is normally transported to the second collection position if the second collection position data is data which indicates that the sample container is positioned at the second collection position, and the transport confirming unit judges that the sample container is not normally transported to the second collection position if the second collection position data is data which indicates that the sample container is not positioned at the second collection position.

5. The transport apparatus according to claim 3, further comprising:
a contact portion confirming unit which confirms whether or not such a state is given that the contact portion is formed between the container transport unit and the sample container, wherein:
the transport confirming unit judges that the sample container is not normally transported to the second collection position irrelevant to contents of the second collection position data, if it is judged by the contact portion confirming unit that the contact portion is not formed.

6. The transport apparatus according to claim 5, wherein the contact portion confirming unit makes the judgment in relation to the formation of the contact portion on the basis of an amount of movement of the container transport unit itself during a period in which the transport is performed by the container transport unit.

7. The transport apparatus according to claim 6, further comprising:
a movement amount detecting unit which is provided at a passage portion for allowing the sample container transported by the container transport unit to pass therethrough between the first collection position and the second collection position and which detects the amount of movement of the sample container in the passage portion, wherein:
the contact portion confirming unit further makes the judgment in relation to the formation of the contact portion on the basis of the amount of movement detected by the movement amount detecting unit.

8. The transport apparatus according to claim 1, wherein at least any one collection position of the first collection position and the second collection position is changeable in a transport direction in which the transport is performed by the container transport unit.

9. The transport apparatus according to claim 3, wherein the container transport unit simultaneously transports the sample container and another sample container by allowing a pressing force to act by making contact with the sample container from a backward position in the transport direction while bringing the sample container and the another sample container different from the sample container in contact with each other at a frontward position in the transport direction of the sample container.

10. The transport apparatus according to claim 9, further comprising:
a contact state detecting unit which detects a contact state between the sample container and the another sample container, wherein:
the transport confirming unit judges that the sample container is not normally transported to the second collection position irrelevant to contents of the second collection position data if an amount of movement of the sample container is different from an amount of movement of the another sample container when the transport is performed by the container transport unit after it is detected by the contact state detecting unit that the sample container and the another sample container are brought in contact with each other.

11. A transport method for transporting a sample as an analysis objective in a state of being accommodated in a sample container, the transport method comprising:
a sample container identifying step of performing individual identification of the sample container to output an identification result thereof as individual identification data;
a first judging step of judging whether or not the sample container is positioned at a first collection position for collecting the sample from the sample container in order to perform a first analysis process to output a judgment result thereof as first collection position data;
a transport step of transporting, from the first collection position to a second collection position, the sample container judged to be positioned at the first collection position in the first judging step by a predetermined transport amount calculated in accordance with the first collection position and the second collection position for collecting the sample from the sample container in order to perform a second analysis process;
a second judging step of judging whether or not the sample container is positioned at the second collection position in relation to the sample container transported in the transport step to output a judgment result thereof as second collection position data; and
a transport confirming step of confirming whether or not the transport of the sample container to the second collection position is adequate on the basis of the first collection position data, the second collection position data, the individual identification data, and data to indicate the predetermined transport amount.

12. The transport method according to claim 11, wherein the individual identification of the sample container in the sample container identifying step is performed on an upstream side from the first collection position in a transport route for the sample container.

13. The transport method according to claim 11, wherein a force to successively transport the sample container to the first collection position and the second collection position is transmitted via a contact portion formed between a transport driving unit and the sample container in the transport step.

14. The transport method according to claim 11, wherein it is judged in the transport confirming step that the sample container is normally transported to the second collection position if the second collection position data is data which indicates that the sample container is positioned at the second collection position, and it is judged in the transport confirming step that the sample container is not normally transported to the second collection position if the second collection position data is data which indicates that the sample container is not positioned at the second collection position.

15. The transport method according to claim 13, further comprising:
a contact portion confirming step of confirming whether or not such a state is given that the contact portion is formed between the transport driving unit and the sample container, wherein:
it is judged in the transport confirming step that the sample container is not normally transported to the second collection position irrelevant to contents of the second collection position data, if it is judged in the contact portion confirming step that the contact portion is not formed.

16. The transport method according to claim 15, wherein the judgment is made in the contact portion confirming step in relation to the formation of the contact portion on the basis of an amount of movement of the transport driving unit itself during a period in which the transport is performed by the transport driving unit.

17. The transport method according to claim 16, further comprising:
a movement amount detecting step of detecting the amount of movement of the sample container in a passage portion, the sample container transported by the transport driving unit being allowed to pass through the passage portion between the first collection position and the second collection position, wherein:

the judgment is made in the contact portion confirming step in relation to the formation of the contact portion on the basis of the amount of movement detected in the movement amount detecting step.

18. The transport method according to claim 11, wherein at least any one collection position of the first collection position and the second collection position is changeable in a transport direction in which the transport is performed by the container transport unit.

19. The transport method according to claim 13, wherein the sample container and another sample container are simultaneously transported in the transport step by allowing a pressing force to act by making contact with the sample container from a backward position in the transport direction while bringing the sample container and the another sample container different from the sample container in contact with each other at a frontward position in the transport direction of the sample container.

20. The transport method according to claim 19, further comprising:

a contact state detecting step of detecting a contact state between the sample container and the another sample container, wherein:

it is judged in the transport confirming step that the sample container is not normally transported to the second collection position irrelevant to contents of the second collection position data if an amount of movement of the sample container is different from an amount of movement of the another sample container when the transport is performed in the container transport step after it is detected in the contact state detecting step that the sample container and the another sample container are brought in contact with each other.

21. A recording medium storing a transport program for transporting a sample as an analysis objective in a state of being accommodated in a sample container by means of a computer, wherein the transport program allows the computer to execute:

a sample container identifying step of performing individual identification of the sample container to output an identification result thereof as individual identification data;

a first judging step of judging whether or not the sample container is positioned at a first collection position for collecting the sample from the sample container in order to perform a first analysis process to output a judgment result thereof as first collection position data;

a transport step of transporting, from the first collection position to a second collection position, the sample container judged to be positioned at the first collection position in the first judging step by a predetermined transport amount calculated in accordance with the first collection position and the second collection position for collecting the sample from the sample container in order to perform a second analysis process;

a second judging step of judging whether or not the sample container is positioned at the second collection position in relation to the sample container transported in the transport step to output a judgment result thereof as second collection position data; and a transport confirming step of confirming whether or not the transport of the sample container to the second collection position is adequate on the basis of the first collection position data, the second collection position data, the individual identification data, and data to indicate the predetermined transport amount.

22. A transport system for transporting a sample as an analysis objective in a state of being accommodated in a sample container between a first analysis apparatus for performing a first predetermined analysis process and a second analysis apparatus for performing a second predetermined analysis process, the transport system comprising:

a first judging unit which judges whether or not the sample container is positioned at a first collection position for collecting the sample from the sample container for the first analysis apparatus and which outputs a judgment result thereof as first collection position data;

a second judging unit which judges whether or not the sample container is positioned at a second collection position for collecting the sample from the sample container for the second analysis apparatus and which outputs a judgment result thereof as second collection position data;

a container transport unit which successively transports the sample container including the sample accommodated therein to the first collection position and the second collection position;

a sample container identification unit which performs individual identification of the sample container in a transport route for the sample container and which outputs an identification result thereof as individual identification data; and a transport confirming unit which confirms whether or not the transport of the sample container to the second collection position is adequate on the basis of the first collection position data, the second collection position data, the individual identification data, and data to indicate a predetermined transport amount calculated in accordance with the first collection position and the second collection position.

* * * * *